(12) United States Patent
Lischinski (10) Patent No.: US 7,938,111 B2
(45) Date of Patent: May 10, 2011

(54) CONNECTION HEAD FOR AN ABSORBER OF AN ANESTHETIC BREATHING SYSTEM

(75) Inventor: Robert Lischinski, Neubrandenburg (DE)

(73) Assignee: Dräger Medical GmbH, Lübeck (DE)

( * ) Notice: Subject to any disclaimer, the term of this patent is extended or adjusted under 35 U.S.C. 154(b) by 687 days.

(21) Appl. No.: 12/041,061

(22) Filed: Mar. 3, 2008

(65) Prior Publication Data

US 2008/0295841 A1    Dec. 4, 2008

(30) Foreign Application Priority Data

Jun. 2, 2007 (DE) .......................... 10 2007 025 808

(51) Int. Cl.
*A61M 11/00* (2006.01)
(52) U.S. Cl. ............................. 128/202.27; 128/205.12
(58) Field of Classification Search ............ 128/202.27, 128/205.12, 205.14, 204.18, 203.12, 205.24, 128/910, 204.22, 203.28
See application file for complete search history.

(56) References Cited

U.S. PATENT DOCUMENTS

| | | | | |
|---|---|---|---|---|
| 3,830,632 A * | 8/1974 | Guzay | ........................... | 422/120 |
| 5,109,838 A * | 5/1992 | Elam | ........................ | 128/203.12 |
| 5,765,550 A * | 6/1998 | Psaros et al. | ............. | 128/202.27 |
| 6,536,430 B1 * | 3/2003 | Smith | ....................... | 128/204.18 |
| 7,487,776 B2 * | 2/2009 | Kleinschmidt | .......... | 128/205.12 |
| 2005/0235994 A1 | 10/2005 | Kleinschmidt | | |

FOREIGN PATENT DOCUMENTS

DE    102004020133 B3    8/2005

* cited by examiner

*Primary Examiner* — Steven O Douglas
(74) *Attorney, Agent, or Firm* — McGlew and Tuttle, P.C.

(57) ABSTRACT

A connection head for an absorber (4) of an anesthetic breathing system has a simple design and can be easily taken apart. A valve device (2) is inserted into a guide sleeve (7), which is open towards the absorber (4). A sealing ring (16), which has two sealing areas (23, 24) and fixes the valve means (2) within the guide sleeve (7), is arranged on the underside of the guide sleeve (7).

15 Claims, 6 Drawing Sheets

Fig. 6

CONNECTION HEAD FOR AN ABSORBER OF AN ANESTHETIC BREATHING SYSTEM

CROSS REFERENCE TO RELATED APPLICATIONS

This application claims the benefit of priority under 35 U.S.C. §119 of German Patent Application 10 2007 025 808.0 filed Jun. 2, 2007, the entire contents of which are incorporated herein by reference.

FIELD OF THE INVENTION

The present invention pertains to a connection head of an anesthetic breathing system with an inner gas duct and with an outer gas duct which is arranged concentrically thereto, in the connection area between an absorber and the connection head.

BACKGROUND OF THE INVENTION

A connection head of the type is known from DE 10 2004 020 133 B3 (corresponding to U.S. application Ser. No. 11/058,624). The connection head is used to connect an absorber cartridge to an anesthetic breathing system or to also replace a used absorber cartridge with a new one even during operation. Valves are used for this purpose within the connection head; on the one hand, these valves bridge over the gas ducts to the absorber in the form of a bypass when the absorber is removed, so that no gas can escape from the anesthetic breathing system. On the other hand, a gas connection is established to the absorber when the absorber cartridge is connected to the connection head.

The valves, which establish or interrupt gas connections, are accommodated in the prior-art connection head in a cylindrical cavity, which is accessible only from the side of the anesthetic breathing system. To clean the valves, the connection head must first be separated from the anesthetic breathing system so that the cover plate fixing the valves can be removed. This makes handling difficult during cleaning, especially because the cover plate is screwed to the housing of the connection head.

SUMMARY OF THE INVENTION

The basic object of the present invention is to improve a connection head of the type mentioned such that it has a simple design and can be easily taken apart.

According to the invention, a connection head is provided for an absorber of an anesthetic breathing system. The connection head comprises a pivotable mount for connecting the absorber to the connection head as well as an inner gas duct in a connection area between the absorber and the connection head and an outer gas duct arranged concentrically to the inner gas duct in the connection area between the absorber and the connection head sleeve, wherein a valve means can be opened towards the absorber. The connection head has a guide sleeve that receives the valve means in the line of the gas ducts. The valve means has a sealing surface for connection to the inner gas duct and a shut-off means in the outer gas duct. The valve means is actuated by the absorber via the sealing surface in such a way that the valve means performs a lifting motion. A sealing ring is provided for connection to the guide sleeve. The sealing ring has a one-piece design with a first sealing area directed towards the outer gas duct and with a second sealing area cooperating with the valve means as the shut-off means. The second sealing area is provided on an underside of the guide sleeve.

The valve means may comprise a hollow cylinder of a stepped design comprising a first cylinder section with a larger cross section forming a ring duct with the guide sleeve, a second cylinder section with a smaller diameter, the second cylinder section being closed off with the sealing surface and a ring section formed between the first cylinder section and the second cylinder section. The ring section forms a valve disk for an inner sealing lip of the sealing ring in the second sealing area. The hollow cylinder may have, at the end facing away from the sealing surface, a flow valve, which opens towards an interior space of the hollow cylinder. The flow valve and the shut-off means may be formed from the inner sealing lip and the ring section and are switched into the opening position with the absorber inserted in the connection head.

A locking means may be provided for fixing the pivotable mount in a use position. The locking means may comprise a barb at the pivotable mount and a locking element. The locking element may be actuated by a release element. The locking element may extend behind the barb and release the barb when the release element is actuated by pressure thereon.

The advantage of the present invention is essentially that the valve means, which switches over the path of the gas when the absorber is inserted into the connection head, is inserted into a guide sleeve, which is open towards the absorber and which is subsequently fixed by a sealing ring, which can be attached to the guide sleeve, within the guide sleeve. The sealing ring has, in a one-piece design, two sealing lips, an outer sealing lip of which, which has a great strain path, lies in contact with an outer valve crater (seat) of the absorber, while an inner sealing lip, which is located in an annular space between the valve means and the guide sleeve, cooperates with an outer ring section of the valve means as a valve disk for the inner sealing lip such that the path of gas through the annular space is interrupted when the absorber has been removed. The ring section lifts off from the inner sealing lip when the absorber is inserted and connected to the connection head, and the path of gas is released.

It is especially advantageous that two sealing areas can be formed due to the one-piece design of the sealing ring and that the corresponding sealing lips can be individually adapted to the particular requirements. For example, the outer sealing lip, which lies on the outer valve crater, must have a great strain path in order to be able to compensate differences in height between the outer valve crater and the guide sleeve. The differences in height are due to manufacturing tolerances between the absorber and the connection head. The inner sealing lip must be such that it possesses good sealing properties together with the outer ring section.

An exemplary embodiment of the present invention is shown in the figures and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
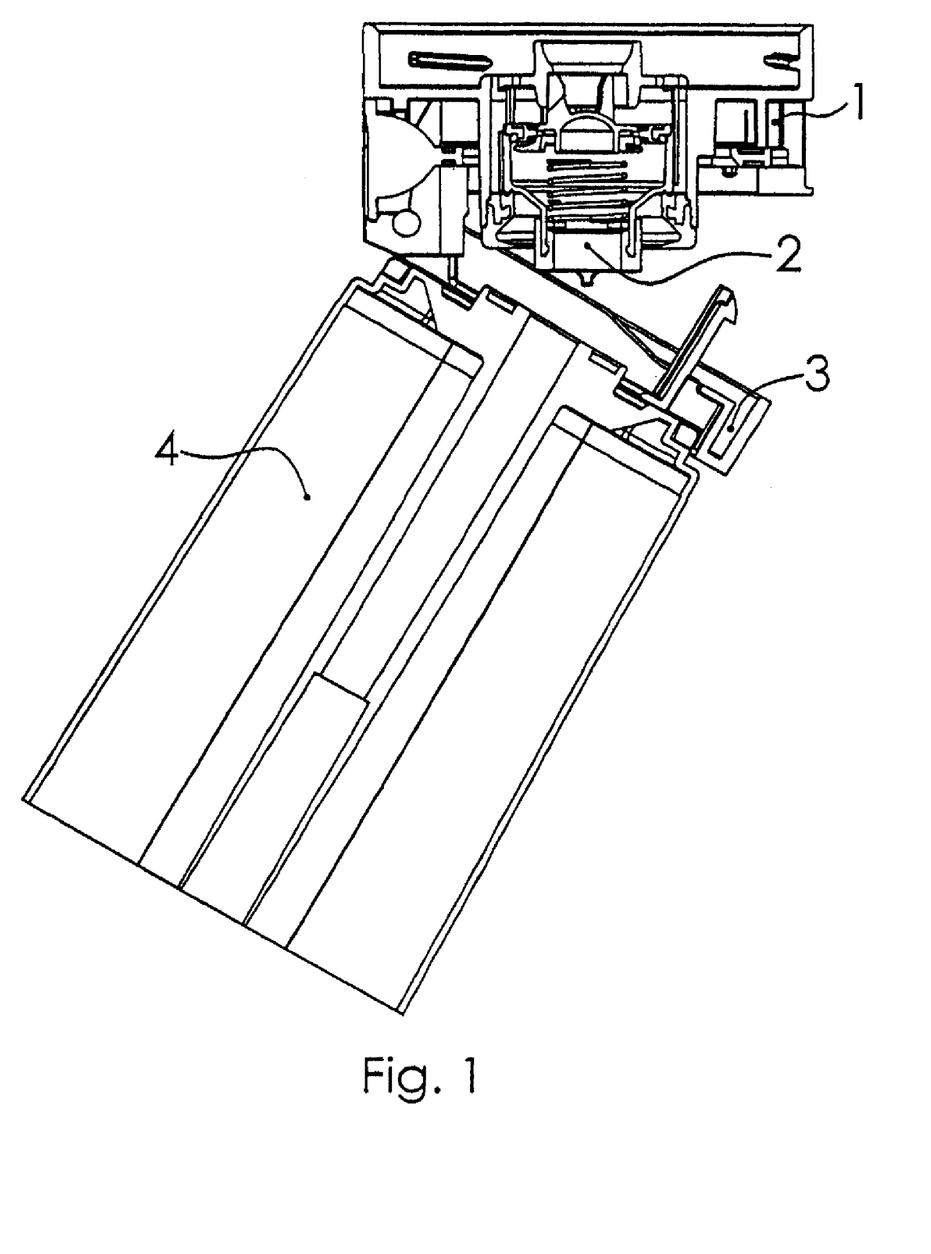
FIG. 1 is a sectional view showing a connection head with an absorber.

Referring to the drawings in particular FIG. 1 schematically shows a longitudinal section of a connection head 1 with a valve means 2 and with an absorber 4 accommodated in a pivotable mount 3.

Figure 2:
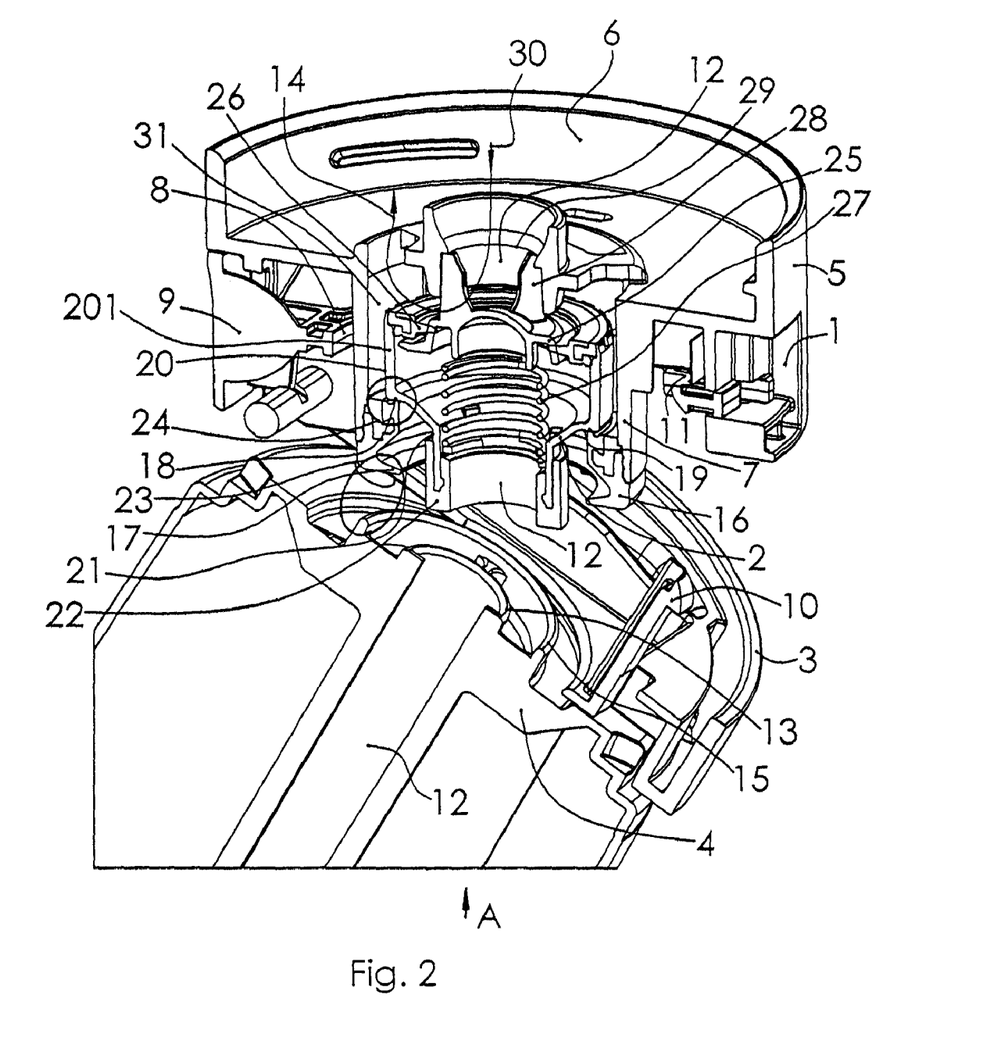
FIG. 2 is a perspective sectional view schematically showing a connection area between the connection head and the absorber according to FIG. 1.

FIG. 2 schematically illustrates the connection area between the connection head 1 and the absorber 4. The connection head 1 has a housing 5 with a connection piece 6 for connection to an anesthetic breathing system, not shown more specifically in FIG. 2; a guide sleeve 7, which accommodates the valve means, and a ring-shaped locking element 8 within the housing 5 with a release button 9.

The mount 3, which receives the absorber 4, has a barb 10, which snaps into a wall section 11 of the locking element 8. To connect the absorber 4 to the connection head 1, the absorber 4 is pushed into the mount 3 and pivoted in the direction of the connection head 1. Reference is made in this connection to DE 10 2004 020 133 B3, which is part of this specification (corresponding to U.S. application Ser. No. 11/058,624, filed Feb. 15, 2005, is also hereby incorporated by reference).

The absorber 4 has an inner gas duct 12 with an inner valve crater 13 and an outer gas duct 14 arranged concentrically thereto with an outer valve crater 15. The gas ducts 12, 14 describe the flow paths through the absorber 4.

The inner gas duct 12 extends within the connection head 1 through the interior space of the valve means 2 and the outer gas duct 14 in an annular space between the valve means 2 and the guide sleeve 7. A sealing ring 16, which has an outer sealing lip 17 directed towards the absorber 4, and an inner sealing lip 18, which is in contact with an outer ring section 19 of the valve means 2, is located on the underside of the guide sleeve 7. The ring section 19 is located between a first cylindrical wall section 20 of the valve means 2 with a larger cross section and a second cylindrical wall section 21 with a smaller diameter, which adjoins same. The wall sections 20, 21 and the ring section 19 together form a valve housing 201 of the valve means 2. The inner sealing lip 18 and the ring section 19 form a second sealing area 24 and are designed to interrupt the flow of gas in the annular space as a shut-off means when the absorber 4 has been removed from the connection head 1.

The second wall section 21 is provided with an elastomer ring 22 at its free end, which extends in the direction of the absorber 4. When the absorber 4 is pivoted in the direction of the connection head 1, the outer sealing lip 17 lies on the outer valve crater 15 and forms a first sealing area 23. The elastomer ring 22 is located in this position of the absorber 4 on the inner valve crater 13.

A flow valve 31 with a valve body 25, which is in contact with a sealing lip 26, is located on the top side of the first wall section 20 of the valve means 2. The valve body 25 is pressed by a compression spring 27 against the sealing lip 26. The valve body 25 is in contact with a projection 29 of the housing 5 via spacers 28. Due to fixation by means of the spacers 28, the valve body 25 always has a fixed position in relation to the housing 5. The flow valve 31 opens when the valve housing 201 is displaced in relation to the valve body 25 in the direction of the spacers 28. In the position of the absorber 4 shown in FIG. 2, the path of gas 30 runs via the inner gas duct 12 through the free spaces between the spacers 28 to the outer gas duct 14.

Figure 3:
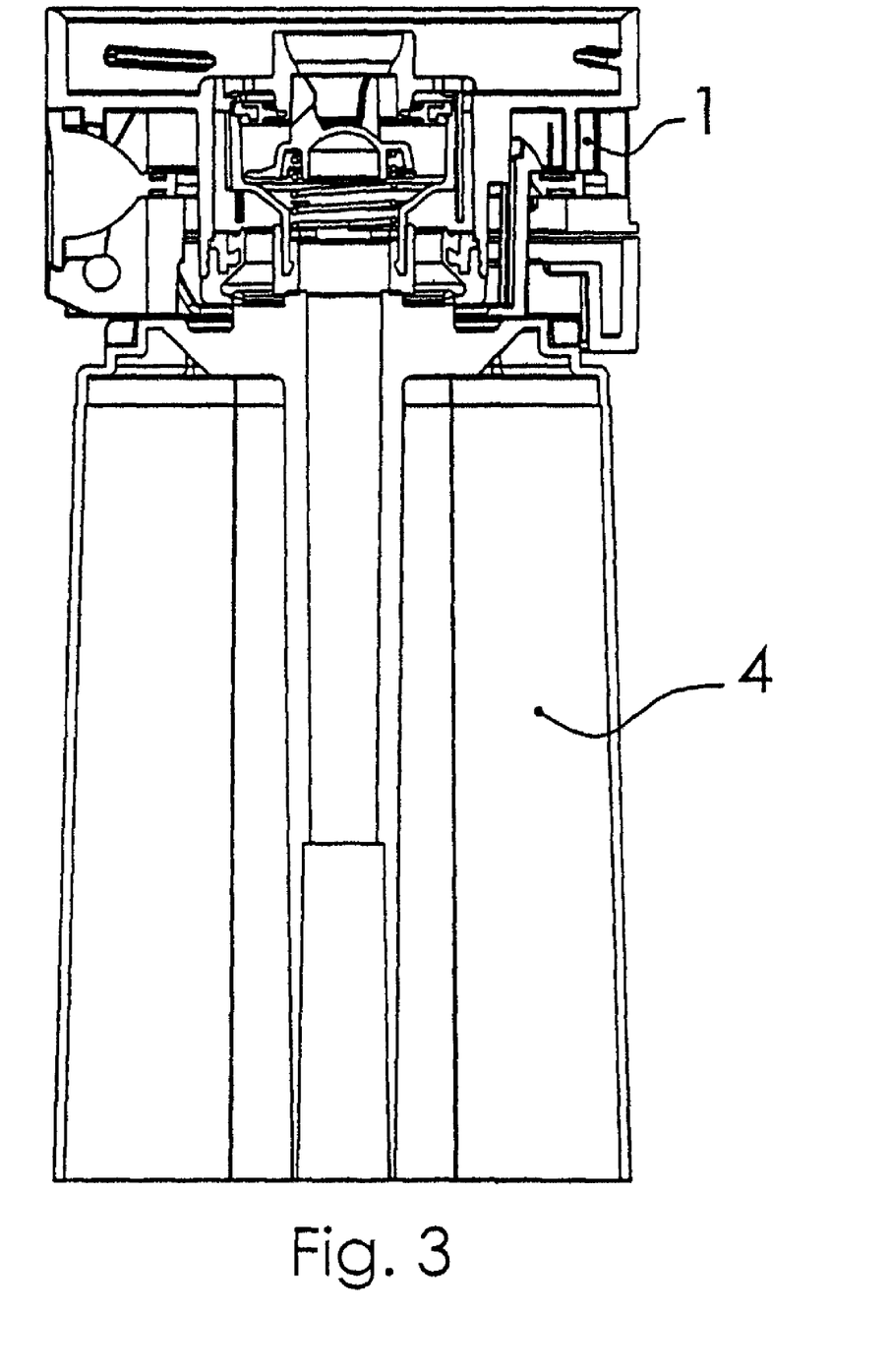
FIG. 3 is a sectional view showing an absorber connected to the connection head.

FIG. 3 shows the connection head 1 with the absorber 4 connected.

Figure 4:
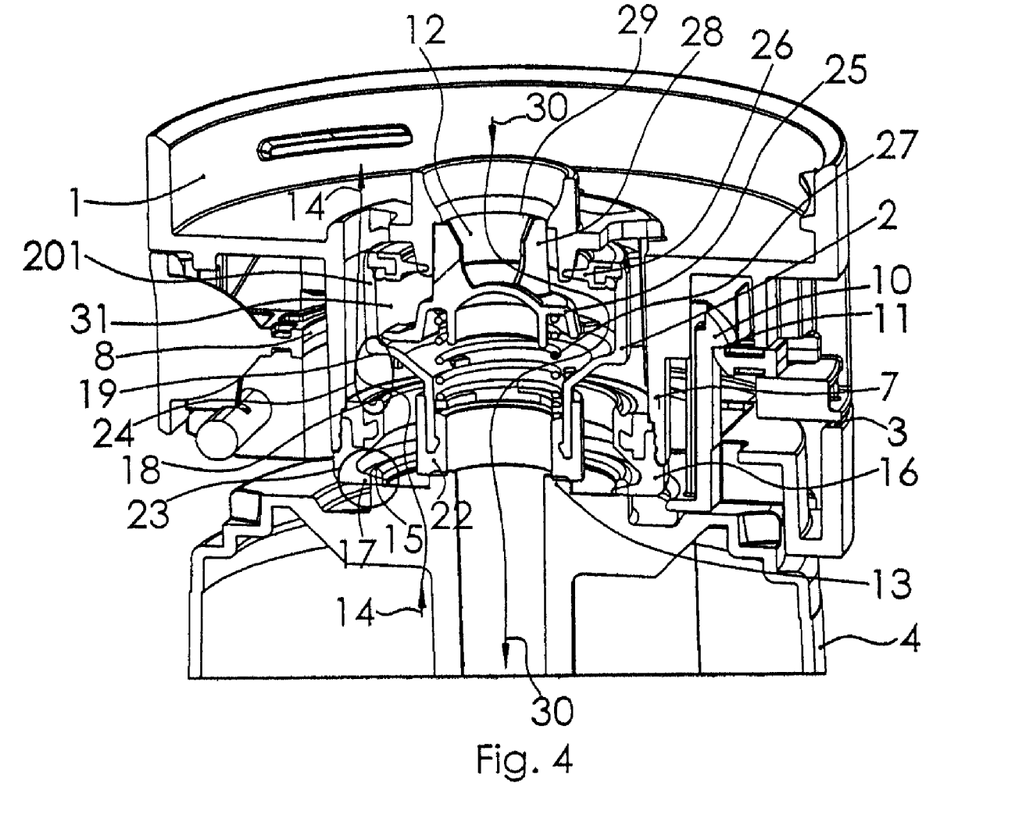
FIG. 4 is perspective sectional view showing the connection area between the connection head and the absorber according to FIG. 3.

FIG. 4 illustrates the connection area between the connection head 1 and the absorber 4, corresponding to FIG. 3, in a longitudinal section. Identical components are designated by the same reference numbers as in FIGS. 1 and 2. In the coupled state, the barb 10 has snapped into the wall section 11 of the spring element 8. The outer valve crater 15 is in contact with the outer sealing lip 17. The inner valve crater 13 is located at the elastomer ring 22 and presses the valve housing 201 of the valve means 2 upward against the force of the compression spring 27. Since the valve body 25 is supported at the projection via the spacers 28 and thus remains in its original position, the sealing lip 26 lifts off from the valve body 25 and the flow valve 31 is opened. At the same time, the ring section 19 separates from the inner sealing lip 18 and the second sealing area 24 is opened. The path of gas 30 from the anesthetic breathing system now leads via the opened flow valve 31 into the inner gas duct 12 and to the absorber 4. The backflow takes place via the outer gas duct 14, the opened second sealing area 24 and the annular gap between the valve means 2 and the guide sleeve 7 back into the anesthetic breathing system. The outer sealing lip 17 is designed as a lip seal with a large deformation area in order to reduce sealing forces, which must be overcome when the mount 3 is coupled with the connection head 1, on the one hand, and to compensate differences in height in the form of manufacturing tolerances, on the other hand.

With the absorber 4 uncoupled, the sealing ring 16 is pulled off from the guide sleeve 7 downward for cleaning purposes and the valve means 2 can be removed and taken apart for cleaning purposes. No tool is necessary for the disassembly. The components of the connection head 1 can be manufactured from plastic according to the injection molding process and can therefore be manufactured at a very low cost as a result.

Figure 5:
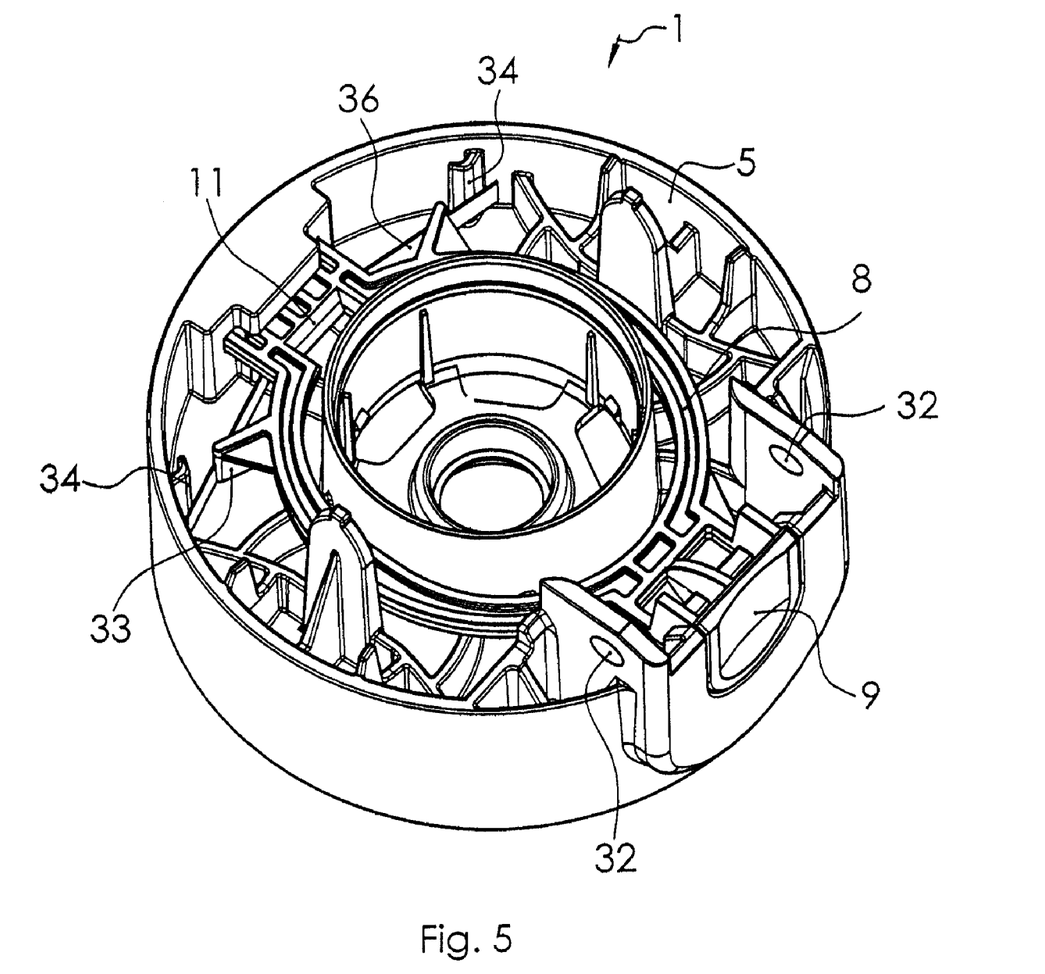
FIG. 5 is a perspective sectional view showing the underside of the connection head with the locking element inserted.

FIG. 5 shows a bottom view of the connection head 1 with the valve means 2 removed and with the mount 3 removed in view "A" according to FIG. 2. The mount 3 is fastened pivotably in the bushes 32 of the housing 5. The locking element 8 has spacing elements 33, which are in contact with a leaf spring 36, the leaf spring 36 being supported on projections 34 of the housing 5.

Figure 6:
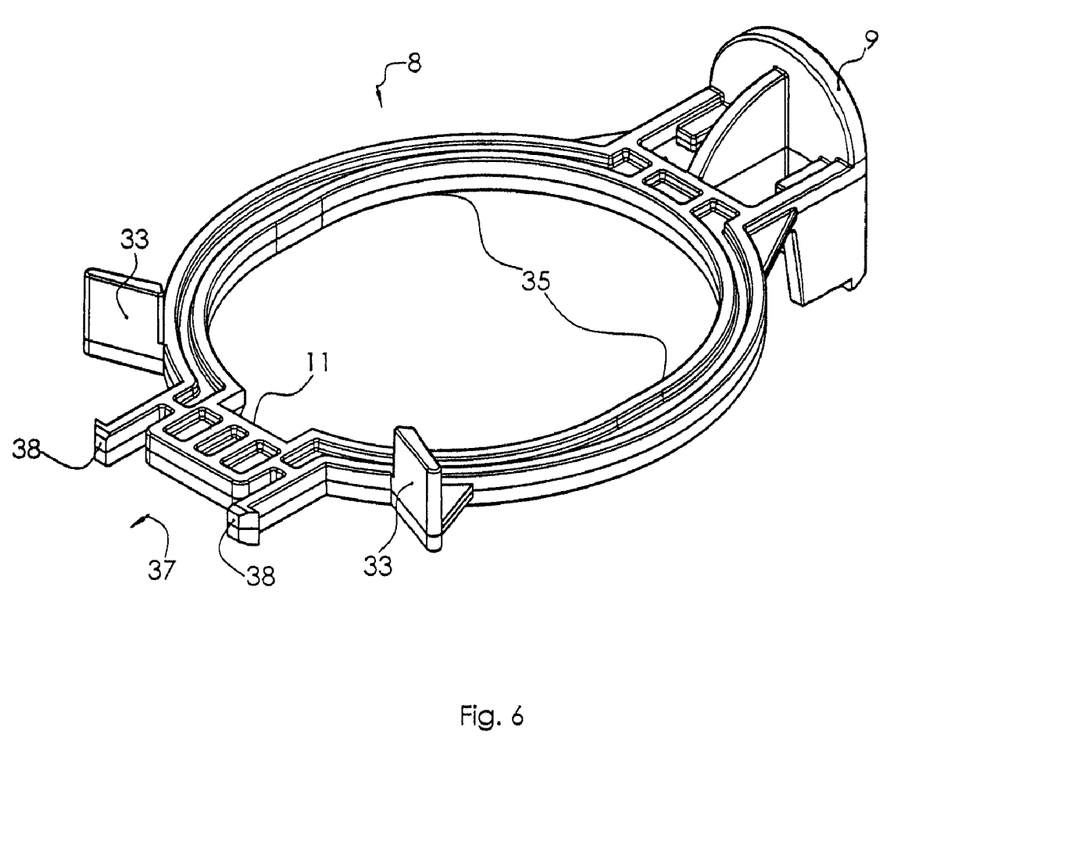
FIG. 6 is a perspective view of the locking element according to FIG. 5.

FIG. 6 illustrates the locking element 8 in a perspective view. The locking element 8 comprises a rigid frame 35, to which the likewise rigid spacing elements 33 are fastened. When applying pressure to the release button 9, the frame 35 and the wall section 11 are displaced in the direction of arrow 37 against the spring force of the leaf spring 36, FIG. 5. The stroke of the locking element 8 is limited by a contact surface 38, which is in contact with the housing 5 at maximum deflection, FIG. 5. When applying pressure to the release button 9, the barb 10, FIG. 2, is released.

While a specific embodiment of the invention has been shown and described in detail to illustrate the application of the principles of the invention, it will be understood that the invention may be embodied otherwise without departing from such principles.

What is claimed is:

1. A connection head for an absorber of an anesthetic breathing system, the connection head comprising:
a pivotable mount for connecting an absorber to said connection head;
an inner gas duct in a connection area between said absorber and said connection head;
an outer gas duct arranged concentrically to said inner gas duct in said connection area between said absorber and said connection head;
a guide sleeve;
a valve means in the line of said gas ducts, said valve means having a sealing surface for connection to said inner gas duct, said valve means having a shut-off means in said outer gas duct, said valve means being actuated by said absorber via said sealing surface in such a way that said valve means performs a lifting motion, said valve means being accommodated in said guide sleeve, which can be opened towards said absorber; and
a sealing ring for connection to said guide sleeve, said sealing ring having a one-piece design with a first sealing area directed towards said outer gas duct and with a second sealing area cooperating with said valve means as said shut-off means, said second sealing area being provided on an underside of said guide sleeve.

2. A connection head in accordance with claim 1, wherein said valve means comprises a hollow cylinder of a stepped design comprising:
a first cylinder section with a larger cross section forming a ring duct with said guide sleeve;
a second cylinder section with a smaller diameter, said second cylinder section being closed off with said sealing surface; and
a ring section formed between said first cylinder section and said second cylinder section as a valve disk for an inner sealing lip of said sealing ring in the second sealing area.

3. A connection head in accordance with claim 2, wherein:
said hollow cylinder has, at the end facing away from said sealing surface, a flow valve, which opens towards an interior space of said hollow cylinder;
said flow valve and said shut-off means are formed from said inner sealing lip and said ring section and are switched into the opening position with said absorber inserted in said connection head.

4. A connection head in accordance with claim 1, further comprising a locking means fixing said pivotable mount in a use position.

5. A connection head in accordance with claim 4, wherein said locking means comprises a barb at said pivotable mount and a locking element, said locking element being actuated by a release element, said locking element extending behind said barb and releasing said barb when said release element is actuated by pressure thereon.

6. A connection head for an absorber of an anesthetic breathing system, the connection head comprising:
a pivotable mount for receiving an absorber in a pivoted out position and for pivoting into a use position for connecting the absorber to said connection head;
an inner gas duct in a connection area between said absorber and said connection head;
an outer gas duct arranged concentrically to said inner gas duct in said connection area between said absorber and said connection head;
a guide sleeve;
a valve means in the line of said gas ducts, said valve means having a sealing surface for connection to said inner gas duct, said valve means having a shut-off means in said outer gas duct, said valve means being actuated by said absorber moving to said use position via said sealing surface in such a way that said valve means performs a lifting motion, said valve means being accommodated in said guide sleeve, which can be opened towards said absorber; and
a sealing ring for connection to said guide sleeve, said sealing ring having a one-piece design with a first sealing area directed towards said outer gas duct and with a second sealing area cooperating with said valve means as said shut-off means, said second sealing area being provided on an underside of said guide sleeve.

7. A connection head in accordance with claim 6, wherein said valve means comprises a hollow cylinder of a stepped design comprising:
a first cylinder section with a larger cross section forming a ring duct with said guide sleeve;
a second cylinder section with a smaller diameter, said second cylinder section being closed off with said sealing surface; and
a ring section formed between said first cylinder section and said second cylinder section as a valve disk for an inner sealing lip of said sealing ring in the second sealing area.

8. A connection head in accordance with claim 7, wherein:
said hollow cylinder has, at the end facing away from said sealing surface, a flow valve, which opens towards an interior space of said hollow cylinder;
said flow valve and said shut-off means are formed from said inner sealing lip and said ring section and are switched into the opening position with said absorber inserted in said connection head.

9. A connection head in accordance with claim 6, further comprising a locking means fixing said pivotable mount in said use position.

10. A connection head in accordance with claim 9, wherein said locking means comprises a barb at said pivotable mount and a locking element, said locking element being actuated by a release element, said locking element extending behind said barb and releasing said barb when said release element is actuated by pressure thereon.

11. A connection head for an absorber of an anesthetic breathing system, the connection head comprising:
an inner gas duct in a connection area between said absorber and said connection head;
an outer gas duct arranged concentrically to said inner gas duct in said connection area between said absorber and said connection head;
a guide sleeve;
a valve means in the line of said gas ducts, said valve means having a sealing surface for connection to said inner gas duct, said valve means having a shut-off means in said outer gas duct, said valve means being actuated by said absorber via said sealing surface in such a way that said valve means performs a lifting motion, said valve means being accommodated in said guide sleeve, which can be opened towards said absorber; and
a sealing ring for connection to said guide sleeve, said sealing ring having a one-piece design with a first sealing area directed towards said outer gas duct and with a second sealing area cooperating with said valve means as said shut-off means, said second sealing area being provided on an underside of said guide sleeve.

12. A connection head in accordance with claim 11, wherein said valve means comprises a hollow cylinder of a stepped design comprising:

a first cylinder section with a larger cross section forming a ring duct with said guide sleeve;

a second cylinder section with a smaller diameter, said second cylinder section being closed off with said sealing surface; and a ring section formed between said first cylinder section and said second cylinder section as a valve disk for an inner sealing lip of said sealing ring in the second sealing area.

13. A connection head in accordance with claim 12, wherein:

said hollow cylinder has, at the end facing away from said sealing surface, a flow valve, which opens towards an interior space of said hollow cylinder;

said flow valve and said shut-off means are formed from said inner sealing lip and said ring section and are switched into the opening position with said absorber inserted in said connection head.

14. A connection head in accordance with claim 11, further comprising:

a pivotable mount for receiving the absorber in a pivoted out position and for pivoting into a use position for connecting the absorber to said connection head; and a locking means fixing said pivotable mount in said use position.

15. A connection head in accordance with claim 14, wherein said locking means comprises a barb at said pivotable mount and a locking element, said locking element being actuated by a release element, said locking element extending behind said barb and releasing said barb when said release element is actuated by pressure thereon.

\* \* \* \* \*